US012766108B2

(12) United States Patent
Xiao et al.

(10) Patent No.: US 12,766,108 B2
(45) Date of Patent: Oct. 20, 2026

(54) FREEZE-DRIED COMPOSITION CONTAINING ANTI-HER2 DRUG CONJUGATE, FREEZE-DRIED PREPARATION AND PREPARATION METHOD THEREFOR AND USE THEREOF

(71) Applicant: NOVOCODEX BIOPHARMACEUTICALS CO., LTD., Shaoxing (CN)

(72) Inventors: Lihai Xiao, Shaoxing (CN); Jiali Chen, Shaoxing (CN); Moutian Ye, Shaoxing (CN); Gang Xia, Shaoxing (CN); Jingjing Zhu, Shaoxing (CN); Lei Fang, Shaoxing (CN); Yuebin Ying, Shaoxing (CN); Luxiong Ye, Shaoxing (CN); Xuejun Liang, Shaoxing (CN)

(73) Assignee: NOVOCODEX BIOPHARMACEUTICALS CO., Shaoxing (CN)

( * ) Notice: Subject to any disclaimer, the term of this patent is extended or adjusted under 35 U.S.C. 154(b) by 299 days.

(21) Appl. No.: 18/576,866

(22) PCT Filed: Jul. 20, 2021

(86) PCT No.: PCT/CN2021/107402

§ 371 (c)(1),
(2) Date: Jan. 5, 2024

(87) PCT Pub. No.: WO2023/000171

PCT Pub. Date: Jan. 26, 2023

(65) Prior Publication Data

US 2024/0245609 A1 Jul. 25, 2024

(51) Int. Cl.

| | |
|---|---|
| ***A61K 9/19*** | (2006.01) |
| ***A61K 47/18*** | (2017.01) |
| ***A61K 47/26*** | (2006.01) |
| ***A61K 47/68*** | (2017.01) |

(52) U.S. Cl.

CPC .............. *A61K 9/19* (2013.01); *A61K 47/183* (2013.01); *A61K 47/26* (2013.01); *A61K 47/68031* (2023.08); *A61K 47/6855* (2017.08)

(58) Field of Classification Search

CPC ........ A61K 9/19; A61K 47/183; A61K 47/26; A61K 47/68031; A61K 47/6855; A61K 9/0019; A61K 47/18

See application file for complete search history.

(56) References Cited

FOREIGN PATENT DOCUMENTS

| | | | |
|---|---|---|---|
| CN | 103717595 A | | 4/2014 |
| CN | 104619351 A | | 5/2015 |
| CN | 111939267 A | | 11/2020 |
| WO | WO2020192693 A1 | * | 10/2020 |

OTHER PUBLICATIONS

Lillian et al. (ARX788, a Site-specific Anti-HER2 Antibody-Drug Conjugate, Demonstrates Potent and Selective Activity in HER2-low and T-DM1-resistant Breast and Gastric Cancers). (Year: 2020).*

International Search Report for PCT/CN201/107402 dated Dec. 1, 2021.

International Written Opinion for PCT/CN2021/107402 dated Dec. 1, 2021.

Lillian S. et al. "ARX788, a Site-specific Anti-HER2 Antibody-Drug Conjugate, Demonstrates Potent and Selective Activity in HER2-low and T-DMI-resistant Breast and Gastric Cancers" Mol. Cancer Therapeutics, vol. 19, No. 9, Sep. 30, 2020 (Sep. 30, 2020), pp. 1833-1843.

* cited by examiner

*Primary Examiner* — Robert A Wax

*Assistant Examiner* — Kimberly Barber

(74) *Attorney, Agent, or Firm* — Lei Fang, Esq.; Smith Tempel Blaha LLC

(57) ABSTRACT

The present invention provides a freeze-dried composition containing anti-HER2 drug conjugate, which comprises ARX788 and one or more of pharmaceutically acceptable lyoprotectant, buffer salts and surfactants, wherein the pH value of the freeze-dried composition is from 5.7 to 6.3. The present invention also provides a freeze-dried preparation containing anti-HER2 drug conjugate and the preparation method thereof. The present invention also provides use of the freeze-dried composition and the freeze-dried preparation. The freeze-dried composition and the freeze-dried preparation provided by the present invention have a very excellent stability, as well as good appearance, short reconstitution time and low moisture content. The product quality is safe and reliable, and the production efficiency is high. The preparation methods of the freeze-dried composition and the freeze-dried preparation provided by the present invention are simple and have low-cost, and they can be used for treating various cancers, and have broad application prospects.

12 Claims, 2 Drawing Sheets

Figure 1:
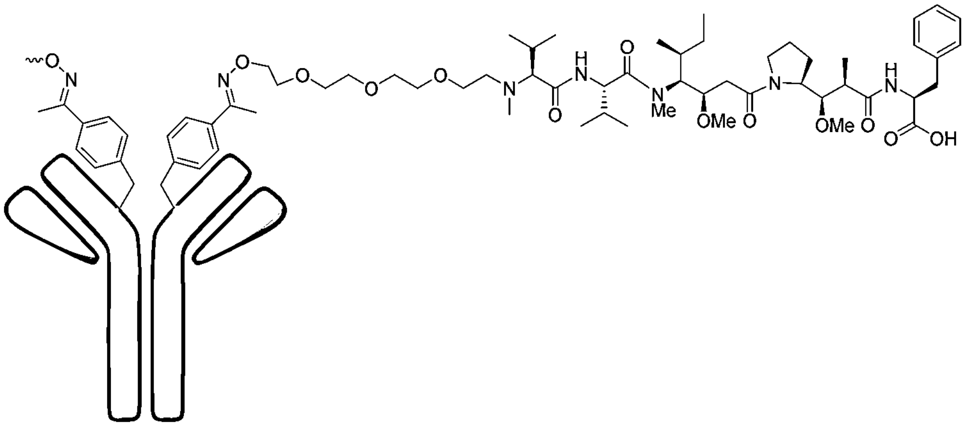

FREEZE-DRIED COMPOSITION CONTAINING ANTI-HER2 DRUG CONJUGATE, FREEZE-DRIED PREPARATION AND PREPARATION METHOD THEREFOR AND USE THEREOF

CROSS-REFERENCE TO RELATED APPLICATIONS

This application is a 371 U.S. National Phase of PCT International Application No. PCT/CN2021/107402 filed on Jul. 20, 2021. The content of which is incorporated herein by reference in its entirety.

TECHNICAL FIELD

The present invention relates to the field of biopharmaceutical technology, in particular to a freeze-dried composition containing anti-HER2 drug conjugate, a freeze-dried preparation prepared from the freeze-dried composition, and a preparation method thereof and use thereof.

BACKGROUND

Human epidermal growth factor receptor 2 (HER2/ErbB2) is a member of the epithelial growth factor receptor family, which is a transmembrane tyrosine kinase. The amplification of HER2 gene exists in about 30% of the primary human breast cancers, and sometimes it is also found in many other solid tumors. The amplification of HER2 gene usually leads to overexpression, resulting in up to one million HER2 protein molecules on the surface of each cancer cell. Increased HER2 protein expression and HER2 gene amplification are associated with poor clinical prognosis, including shortened relapse-free survivals and overall survivals (OSs) of breast cancer and gastric cancer, and shortened overall survivals of lung cancer, ovarian cancer, colon cancer and pancreatic cancer. Several therapeutic agents, antibodies and antibody-drug conjugates (ADCs, including T-DM1) targeting HER2 have been proved to have clinical anticancer activity.

A pharmaceutical must be marketed in the form of final preparation, and the selection of dosage form, the types and dosages of excipients, and the preparation process all have an impact on the stability of the product. A qualified product should have stable and controllable quality within its validity period, and be convenient for transportation, storage and clinical use. Pharmaceutical stability is one of the important indicators for evaluating pharmaceutical effectiveness and safety. Stability research is the main basis for determining the storage condition and shelf life of a pharmaceutical, which can also provide scientific basis for the pharmaceutical production, packaging, transportation condition and so on. For a pharmaceutical, especially a biological product, the maintenance of molecular configuration and biological activity of the active ingredient depends on various covalent and non-covalent forces, and the maintenance of these forces are closely related to the microenvironment they are in, such as temperature, light, ion concentration, and mechanical shear force.

ADC is a highly effective and specific pharmaceutical used to treat cancers and other diseases, in which the antibody part specifically binds to the antigen thereof on the target cells, allowing the drug to exert its cytotoxicity or other therapeutic effects on the target cells. However, like other protein pharmaceuticals, the antibody is prone to degradation, such as through oxidation, deamidation and fragmentation, as well as to form particles and aggregates. The purpose of developing an ADC formulation is to ensure stable administration to patients and reliable quality. However, compared with naked antibody, ADC has a more complex structure and has more unstable factors. The numerous formulation characteristics which are exhibited during the development process of a biological preparation may affect the safety, effectiveness and quality controllability of the product. Therefore, ADC poses a challenge to the preparation used for therapeutic purpose. In order to provide a stable ADC pharmaceutical during transportation and storage, careful selections of the carrier, excipient, and/or stabilizer in the pharmaceutical preparation are necessary.

The ADC quality attribute includes the aspect of free small molecule drug, and the aspect of naked antibody, as well as the aspect of antibody drug conjugate. The content of free payload may affect the safety of the ADC, while the naked antibody itself has inherent critical quality attribute of an antibody, such as chemical instability, like aggregation, fragmentation, charge heterogeneity, degradation, oxidation and so on, which may affect a variety of clinical effects such as biological activity, immunogenicity, drug efficacy and safety. The unique quality attribute of an ADC, such as chemical stability and drug-antibody ratio of the conjugate, may affect the efficacy, drug metabolism and safety of the ADC.

SUMMARY

Based on the particularity of an ADC preparation, in order to provide a novel and stable ADC preparation, one object of the present invention is to provide a freeze-dried composition containing anti-HER2 drug conjugate.

Another object of the present invention is to provide a freeze-dried preparation containing anti-HER2 drug conjugate and a preparation method thereof.

Further object of the present invention is to provide use of the freeze-dried composition and the freeze-dried preparation.

The freeze-dried composition containing anti-HER2 drug conjugate provided by the present invention comprises ARX788 and one or more of pharmaceutically acceptable lyoprotectant, buffer salt and surfactant, wherein the pH value of the freeze-dried composition is from 5.7 to 6.3.

In some preferred embodiments, the pH value of the freeze-dried composition may be from 6.0 to 6.3, and in some most preferred embodiments, the pH value of the freeze-dried composition may be 6.0.

ARX788 described in the present invention is an anti-HER2 ADC, also known as anti-HER2 monoclonal antibody AS269 conjugate (the structural formula thereof is shown in FIG. 1). In ARX788, the anti-HER2 antibody is obtained by using codon expansion technology to mutate the amino acid at 121st position of each heavy chain of trastuzumab into a p-acetyl phenylalanine residue, which is then subjected to oximation reaction with a small molecule toxin containing a hydroxylamine group for fixed coupling to give the product with a main drug-to-antibody ratio of 1:2. Chinese patent CN 201280036296.1 provides a detailed description of this.

The pharmaceutically acceptable lyoprotectant, buffer salt and surfactant described in the present invention may be any type commonly used in pharmaceutical field, especially those commonly used in ADC preparations. In some preferred embodiments, the buffer salt includes but is not limited to acetate, phosphate, citrate, histidine salt, succinate, 2-(N-morpholinyl) ethanesulfonic acid, edetate disodium, etc: the surfactant includes but is not limited to polysorbate 20, polysorbate 80, etc: the lyoprotectant includes but is not limited to sucrose, trehalose, etc.

In some preferred embodiments, the freeze-dried composition described in the present invention comprises 10 mg/mL to 30 mg/mL of ARX788, 5 mM to 10 mM of histidine, 2.5 wt. % to 8 wt. % trehalose and 0.01 wt. % to 0.05 wt. % of polysorbate 80.

In some more preferred embodiments, the freeze-dried composition described in the present invention comprises 20 mg/mL of ARX788, 5 mM of histidine, 6 wt. % trehalose and 0.02 wt. % of polysorbate 80, and the pH of the freeze-dried composition is 6.0.

The present invention also provides a freeze-dried preparation containing anti-HER2 drug conjugate, which is prepared from the freeze-dried composition described in any one of the above technical solutions.

The present invention also provides a preparation method for the freeze-dried preparation, comprising the following steps:

S1: prefreezing the freeze-dried composition described in any one of the above technical solutions at −50° C. to −40° C. for 3 hours to 6 hours;

S2: heating up the freeze-dried composition after treated in step S1 to −25° C. to −20° C. and holding at this temperature and a vacuum degree of 10 Pa to 15 Pa for 30 hours to 50 hours; and S3: heating up the freeze-dried composition after treated in step S2 to 25° C. to 30° C. and holding at this temperature and a vacuum degree of 10 Pa to 15 Pa for 5 hours to 10 hours.

In some preferred embodiments, in the preparation method provided by the present invention, the step S1 comprises: cooling down the freeze-dried composition described in any one of the above technical solutions to 2° C. to 5° C. within 0.5 hour to 1.5 hours and holding at the same temperature for 0.5 hour to 1.5 hours, then cooling down to −50° C. to −40° C. within 3 hours to 5 hours and holding at the same temperature for 3 hours to 6 hours. In some more preferred embodiments, the step S1 comprises: cooling down the freeze-dried composition described in any one of the above technical solutions to 4° C. within 1 hour and holding at the same temperature for 1 hour, then cooling down to −45° C. within 3.5 hours and holding at the same temperature for 5 hours.

In some preferred embodiments, in the preparation method provided by the present invention, the step S2 comprises: heating up the freeze-dried composition after treated in step S1 to −23° C. to −20° C. within 0.2 hour to 0.8 hour and holding at the same temperature and a vacuum degree of 12 Pa to 14 Pa for 35 hours to 45 hours. In some more preferred embodiments, the step S2 comprises: heating up the freeze-dried composition after treated in step S1 to −23° C. to −20° C. within 0.5 hour and holding at the same temperature and a vacuum degree of 13 Pa for 40 hours.

In some preferred embodiments, in the preparation method provided by the present invention, the step S3 comprises: heating up the freeze-dried composition after treated in step S2 to 25° C. to 30° C. within 2 hours to 8 hours and holding at the same temperature and a vacuum degree of 12 Pa to 14 Pa for 5 hours to 10 hours. In some more preferred embodiments, the step S3 comprises: heating up the freeze-dried composition after treated in step S2 to 25° C. to 30° C. within 5 hours and holding at the same temperature and a vacuum degree of 13 Pa for 8 hours.

The present invention also provides use of the freeze-dried composition described in any one of the above technical solutions or the freeze-dried preparation described in any one of the above technical solutions for the preparation of a medicament for treating a cancer.

In the use of the present invention, the cancer includes but is not limited to breast cancer, gastric cancer, lung cancer, ovarian cancer, colorectal cancer, urothelial cancer, biliary tract cancer, liver cancer, brain cancer, esophageal cancer, endometrial cancer, uterine cancer, kidney cancer, bladder cancer, thyroid cancer, salivary gland cancer or pancreatic cancer.

The freeze-dried composition and the freeze-dried preparation provided by the present invention are specifically designed for the novel ADC drug ARX788. By setting specific pH value, composition formula and even freeze-drying process, the drop of the small molecule drug and the decline of CEX main peak can be effectively reduced. The resulting freeze-dried product has very excellent stability and can maintain good stability and biological activity for a long time even at high temperatures (such as 40° C.). Moreover, the freeze-dried product also has good appearance, short reconstitution time (within one minute, even up to within 30 seconds) and low moisture content. The product quality is safe and reliable, and the production efficiency is high. The preparation methods of the freeze-dried composition and the freeze-dried preparation provided by the present invention are simple and have low-cost, and they can be used for treating various cancers, and have broad application prospects.

BRIEF DESCRIPTIONS OF THE DRAWINGS

FIG. 1 shows the structure diagram of ADC drug ARX788, wherein one antibody protein is coupled with two small molecule compounds.

Figure 2A:
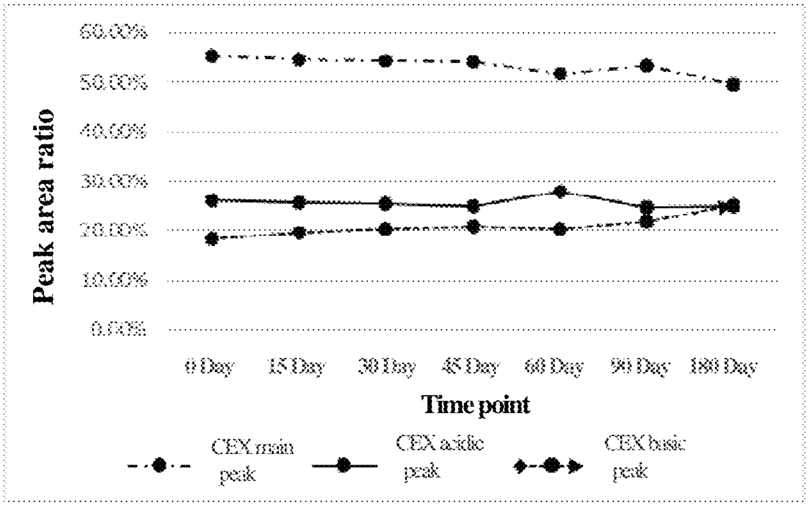
Figure 2B:
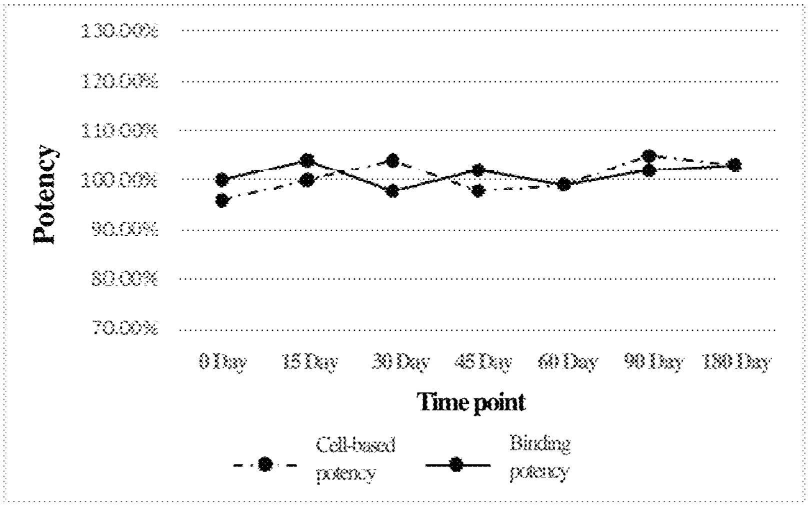

FIG. 2A and FIG. 2B respectively show the charts of CEX changing trend and potency changing trend under the investigation with high temperature condition in Example 5.

DETAILED DESCRIPTIONS

The technical solutions of the present invention will be further described in detail below in combined with specific examples.

The ADC drug ARX788 and ADC reference substance (RS) used in the examples are provided by Zhejiang Novocodex Biopharmaceuticals Co., Ltd. Other reagents or raw materials are commercially available if not particularly indicated.

The test items and test conditions used in the examples are described as follows:

Appearance: measured by visual inspection with clarity detector.

Protein concentration: measured by Cary 100 UV-VIS spectrophotometer.

pH value: instrument: Mettler InLab® Micro Pro pH meter.

Cation-Exchange Chromatography CEX-HPLC:

| | |
|---|---|
| Chromatographic column | Dionex BioLC ProPac WCX-10, 4 × 250 mm 10 μm |
| Detector wavelength | 280 nm |
| Temperature of temperature-controlled oven | 40° C. |
| Auto-Sampler temperature | 5° C. |
| Flow rate | 1.0 mL/min |
| Injection volume | 100 μL |

-continued

| | | | |
|---|---|---|---|
| Mobile phase A | 20 mM $NaH_2PO_4$•$2H_2O$, pH 6.5 ± 0.1 | | |
| Mobile phase B | 20 mM $NaH_2PO_4$•$2H_2O$, 200 m M NaCl, pH 6.5 ± 0.1 | | |
| Gradient elution | Time (min) | A % | B % |
| | 0 | 90 | 10 |
| | 5 | 90 | 10 |
| | 75 | 60 | 40 |
| | 80 | 60 | 40 |
| | 82 | 0 | 100 |
| | 85 | 0 | 100 |
| | 87 | 90 | 10 |
| | 100 | 90 | 10 |

Residual Amount of AS269 (Small Molecule Toxin):

| | | | |
|---|---|---|---|
| Chromatographic column | Waters XBridge Shield RP 18, 3.5 μm, 1*100 mm | | |
| Detector wavelength | 214 nm | | |
| Temperature of temperature-controlled oven | 40° C. | | |
| Auto-Sampler temperature | 5° C. | | |
| Flow rate | 0.8 mL/min | | |
| Injection volume | 100 μL | | |
| Mobile phase A | 0.1% TFA/water | | |
| Mobile phase B | 0.1% TFA/ACN | | |
| Gradient elution | Time (min) | A % | B % |
| | 0 | 80 | 20 |
| | 9 | 60 | 40 |
| | 12 | 20 | 80 |
| | 12.1 | 80 | 20 |
| | 15 | 80 | 20 |

Cell-Based Potency Test:

The cell-based potency of the freeze-dried sample relative to RS was tested by using BT-474 cell line (ATCC, article No. HTB-20).

The specific process was as follows: BT-474 cells were cultured to obtain a sufficient quantity with ATCC Hybrid Care Medium (ATCC, article No. 46-X) containing 10% fetal bovine serum (Gibco, article No. 10099141) under the conditions of 37° C. and 5% carbon dioxide. $1.5\times10^4$ of BT-474 cells were inoculated into each well in a 96-well cell culture plate (Corning, article No. 3599), with an amount of 80 μL/well. The freeze-dried sample and RS were subjected to gradient dilution from 55.8 μg/mL to 0.2 μg/mL, with a total of 10 concentrations and 2 parallel wells for each dilution. The diluted freeze-dried sample and RS were transferred to the culture plate inoculated with BT-474 cells, with an amount of 10 μL per well, and the plate was cultured under the conditions of 37° C. and 5% carbon dioxide. 10 μL of CCK-8 (Beyotime, article No. C0043) test reagent was added into each well at day 5 for coloration under the conditions of 37° C. and 5% carbon dioxide for 6 hours. The optical density values were read by a microplate reader at 450 nm and 620 nm wavelengths. EC50 of the freeze-dried sample and RS were calculated by using SoftMax Pro software, and the relative cell-based potency of the freeze-dried sample was calculated by using the following formula: relative cell-based potency (%)=(EC50 RS)/(EC50 freeze-dried sample)×100%.

Binding Potency Test:

ELISA was used to test the binding potency of the freeze-dried sample relative to RS.

The specific process was as follows: HER2 antigen (R&D, article No. 1129-ER-050) was added into a 96-well plate (Corning, article No. 9018) with an amount of 50 μL/well to be coated overnight at 2° C. to 8° C. Blocking solution (Fisher Scientific, article No. 37528) was added with an amount of 200 μL/well, and the plate was shaken at 200±10 rpm for 60 minutes at room temperature. In the 96-well plate, the freeze-dried sample and RS were subjected to gradient dilution from 10 μg/mL to 0.00017 μg/mL by using the blocking solution, with a total of 11 concentrations and 2 parallel wells for each dilution, and the plate was shaken at 200±10 rpm for 60 minutes at room temperature. Second antibody (Abcam, article No. ab79115) was added with an amount of 50 μL/well, and the plate was shaken at 200±10 rpm for 60 minutes at room temperature. TMB coloring solution (Beyotime, article No. P0209) was added with an amount of 50 μL/well, and the plate was shaken at 200±10 rpm for 10 minutes at room temperature. 5% sulfuric acid was added with an amount of 50 μL/well for termination, and the light absorbance values were read at 450 nm and 620 nm respectively. EC50 of the freeze-dried sample and RS were calculated by using SoftMax Pro software, and the relative binding potency of the freeze-dried sample was calculated by using the following formula: relative binding potency (%)=(EC50 RS)/(EC50 freeze-dried sample)×100%.

Unless otherwise specified, the percentages used in the examples are all mass percentages.

Example 1 Stability Study Under Different pH Values

Formulations 1 to 10 with different pH values were designed (see Table 1).

TABLE 1

Formulations with different pH values

| Formulation number | Anti-HER2 ADC concentration | Buffer salt type | Buffer salt concentration | Trehalose concentration | Polysorbate 80 concentration | pH value |
|---|---|---|---|---|---|---|
| Formulation 1 | 10 mg/ml | Histidine salt | 5 mM | 50 mg/ml | 0.2 mg/ml | 5.4 |
| Formulation 2 | | | | | | 5.7 |
| Formulation 3 | | | | | | 6.0 |
| Formulation 4 | | | | | | 6.3 |
| Formulation 5 | | | | | | 7.2 |
| Formulation 6 | | Acetate | | | | 4.0 |
| Formulation 7 | | | | | | 4.5 |
| Formulation 8 | | | | | | 5.0 |
| Formulation 9 | | | | | | 5.5 |
| Formulation 10 | | | | | | 6.0 |

Samples Preparation:

(1) 5 mM acetate buffer solution and histidine salt buffer solution were prepared respectively, and adjusted to the target pH values with hydrochloric acid or sodium hydroxide.

(2) Excipient stock solutions were prepared by using the buffer salt solutions, with the polysorbate 80 concentration of 14 mg/ml (70 times of the target concentration) and the trehalose concentration of 500 mg/ml (10 times of the target concentration) respectively.

(3) 10 ADC solutions were taken and added into pretreated ultrafiltration centrifuge tubes (model: 30 k, 15 ml) respectively. The tubes were centrifuged for 20 minutes, then added with the buffer salt solutions and centrifuged for another 20 minutes for solution replacement. The solution replacement and concentration operations were repeated four times to give ADC concentrated solutions containing target buffer salts.

(4) The protein concentrations of the ADC solutions after solution replacement and concentration were measured. The excipient concentrated solutions with corresponding amounts were added according to the calculated values, and the buffer salts were added to the target volume.

(5) The samples were subjected to filtration, subpackaging and then plugging and capping.

Stability Investigation:

The samples were placed at 25° C. for a total of 2 months investigation. The investigation results are shown in Table 2, wherein TO represents the time point at which the samples began to be placed, 25° C.-1M represents the time point at which the samples were placed for one month, and 25° C.-2M represents the time point at which the samples were placed for two months.

TABLE 2

Summary of stability investigation results for the formulations with different pH values

| Formulation number | Time point | Appearance | Protein concentration (mg/ml) | pH value | CEX-HPLC(%) Main peak | CEX-HPLC(%) Acidic peak | CEX-HPLC(%) Basic peak | AS269 residue (%) |
|---|---|---|---|---|---|---|---|---|
| Formulation 1 | T0 | Colorless and no visible foreign matter | 9.353 | 5.457 | 57.65 | 28.19 | 14.16 | 0.018 |
| | 25° C.-1 M | Colorless and no visible foreign matter | 10.215 | 5.528 | 51.44 | 24.36 | 24.21 | 0.036 |
| | 25° C.-2 M | Colorless and no visible foreign matter | 10.090 | 5.513 | 42.16 | 24.87 | 32.97 | 0.028 |
| Formulation 2 | T0 | Colorless and no visible foreign matter | 9.064 | 5.727 | 58.13 | 28.7 | 13.17 | <0.017 |
| | 25° C.-1 M | Colorless and no visible foreign matter | 10.006 | 5.802 | 49.26 | 27.64 | 23.11 | 0.021 |
| | 25° C.-2 M | Colorless and no visible foreign matter | 10.001 | 5.745 | 41.93 | 29.39 | 28.67 | 0.039 |
| Formulation 3 | T0 | Colorless and no visible foreign matter | 9.303 | 5.976 | 59.08 | 29.33 | 11.58 | <0.017 |
| | 25° C.-1 M | Colorless and no visible foreign matter | 10.333 | 6.077 | 46.8 | 31.70 | 21.49 | <0.015 |
| | 25° C.-2 M | Colorless and no visible foreign matter | 10.383 | 6.005 | 36.58 | 38.36 | 25.05 | 0.023 |
| Formulation 4 | T0 | Colorless and no visible foreign matter | 9.031 | 6.31 | 58.44 | 29.86 | 11.69 | <0.016 |
| | 25° C.-1 M | Colorless and no visible foreign matter | 10.124 | 6.428 | 41.26 | 39.55 | 19.18 | <0.015 |
| | 25° C.-2 M | Colorless and no visible foreign matter | 10.077 | 6.344 | 30.81 | 49.58 | 19.6 | 0.018 |
| Formulation 5 | T0 | Colorless and no visible foreign matter | 10.515 | 7.189 | 57.67 | 29.10 | 13.23 | <0.016 |
| | 25° C.-1 M | Colorless and no visible foreign matter | 10.090 | 7.201 | 30.90 | 52.50 | 16.60 | <0.016 |
| | 25° C.-2 M | Colorless and no visible foreign matter | 9.989 | 7.194 | 22.47 | 61.49 | 19.05 | <0.016 |

TABLE 2-continued

Summary of stability investigation results for the formulations with different pH values

| Formulation number | Time point | Appearance | Protein concentration (mg/ml) | pH value | CEX-HPLC(%) Main peak | Acidic peak | Basic peak | AS269 residue (%) |
|---|---|---|---|---|---|---|---|---|
| Formulation 6 | T0 | Colorless and no visible foreign matter | 9.872 | 3.982 | 57.71 | 26.94 | 15.34 | <0.016 |
| | 25° C.-1 M | Colorless and no visible foreign matter | 10.329 | 3.958 | ND | ND | ND | 0.18 |
| | 25° C.-2 M | Colorless and no visible foreign matter | 10.192 | 3.988 | ND | ND | ND | 0.234 |
| Formulation 7 | T0 | Colorless and no visible foreign matter | 9.804 | 4.531 | 56.93 | 27.53 | 15.53 | <0.016 |
| | 25° C.-1 M | Colorless and no visible foreign matter | 10.330 | 4.495 | ND | ND | ND | 0.111 |
| | 25° C.-2 M | Colorless and no visible foreign matter | 10.211 | 4.526 | ND | ND | ND | 0.154 |
| Formulation 8 | T0 | Colorless and no visible foreign matter | 9.505 | 5.02 | 56.91 | 27.29 | 15.79 | <0.016 |
| | 25° C.-1 M | Colorless and no visible foreign matter | 9.920 | 4.983 | ND | ND | ND | 0.055 |
| | 25° C.-2 M | Colorless and no visible foreign matter | 9.878 | 5.031 | ND | ND | ND | 0.083 |
| Formulation 9 | T0 | Colorless and no visible foreign matter | 9.846 | 5.536 | 56.3 | 28.71 | 14.98 | <0.016 |
| | 25° C.-1 M | Colorless and no visible foreign matter | 10.366 | 5.511 | 46.53 | 22.96 | 30.51 | 0.026 |
| | 25° C.-2 M | Colorless and no visible foreign matter | 10.259 | 5.56 | 37.28 | 23.68 | 39.02 | 0.038 |
| Formulation 10 | T0 | Colorless and no visible foreign matter | 9.977 | 6.037 | 57.56 | 27.33 | 15.1 | <0.016 |
| | 25° C.-1 M | Colorless and no visible foreign matter | 10.460 | 6.030 | 47.88 | 28.98 | 23.13 | <0.015 |
| | 25° C.-2 M | Colorless and no visible foreign matter | 10.225 | 6.090 | 36.85 | 35.38 | 27.78 | 0.016 |

ND: due to significant increase in AS269 residue at this time point, CEX was not tested.

Result Analysis:

According to the AS269 residue results (Table 2), except for formulation 3 (pH 6.0), formulation 4 (pH 6.3) and formulation 10 (pH 6.0), the growth trend of AS269 residue is observed in all other formulations (pH<6.0) under the investigation at 25° C. The lower the pH is, the higher the AS269 residue is, indicating that the small molecule is prone to drop under the condition that pH is less than 6.0.

According to the CEX results, the decline of CEX main peak as well as the increase of acidic peak and basic peak are more likely to happen under the condition of pH>6.0.

It can be seen that the pH value of the freeze-dried composition is crucial for product stability. The pH value of the freeze-dried composition of the present invention is preferably between 5.7 and 6.3, more preferably around 6.0.

Example 2 Formulation Stability Study Under Different ADC Concentrations and Polysorbate 80 Concentrations According to the experimental results of Example 1, formulations 11-22 (Table 3) were designed to investigate the effect of different ADC concentrations and different polysorbate 80 concentrations on product stability. After placing the samples under the conditions of 25° C. and shaking at 200 rpm for 1 day and 3 days respectively, samples were taken for testing. The test results (Table 4) show that there are no significant changes in all indicators of the samples of the formulations 11-22 before and after shaking. Therefore, under the pH value of approximately 6.0, with the protein concentration of 5 mg/mL to 30 mg/ml and the polysorbate 80 concentration range of 0.01% to 0.05%, the protein stabilities are all good.

TABLE 3

Formulations with different ADC concentrations and polysorbate 80 concentrations

| Formulation number | Trehalose concentration | Buffer salt | pH value | Anti-HER2 ADC concentration | Polysorbate 80 concentration |
|---|---|---|---|---|---|
| Formulation 11 | 5% | 5 mM histidine salt | 6.0 | 5 mg/ml | 0.01% |
| Formulation 12 | | | | | 0.02% |
| Formulation 13 | | | | | 0.05% |
| Formulation 14 | | | | 10 mg/ml | 0.01% |
| Formulation 15 | | | | | 0.02% |
| Formulation 16 | | | | | 0.05% |
| Formulation 17 | | | | 20 mg/ml | 0.01% |
| Formulation 18 | | | | | 0.02% |
| Formulation 19 | | | | | 0.05% |
| Formulation 20 | | | | 30 mg/ml | 0.01% |
| Formulation 21 | | | | | 0.02% |
| Formulation 22 | | | | | 0.05% |

TABLE 4

Summary of shaking stability results for the formulations with different ADC concentrations and polysorbate 80 concentrations

| | | | Protein | | CEX-HPLC(%) | | | AS269 |
|---|---|---|---|---|---|---|---|---|
| Formulation number | Time point | Appearance | concentration (mg/ml) | pH value | Main peak | Acidic peak | Basic peak | residue (%) |
| Formulation 11 | T0 | Colourless and no visible foreign matter | 5.20 | 6.007 | 62.50 | 27.10 | 10.40 | 0.031 |
| | Shaking for 1 day | Colorless and no visible foreign matter | 5.00 | 6.030 | 60.70 | 28.60 | 10.70 | 0.031 |
| | Shaking for 3 days | Colorless and no visible foreign matter | 5.42 | 5.989 | 61.00 | 28.00 | 11.10 | 0.031 |
| Formulation 12 | T0 | Colorless and no visible foreign matter | 5.30 | 6.065 | 62.30 | 27.20 | 10.50 | 0.031 |
| | Shaking for 1 day | Colorless and no visible foreign matter | 5.13 | 6.003 | 60.00 | 29.10 | 10.90 | 0.031 |
| | Shaking for 3 days | Colorless and no visible foreign matter | 5.30 | 6.043 | 60.40 | 28.30 | 11.20 | 0.031 |
| Formulation 13 | T0 | Colorless and no visible foreign matter | 5.30 | 5.987 | 62.00 | 27.30 | 10.70 | 0.031 |
| | Shaking for 1 day | Colorless and no visible foreign matter | 5.22 | 6.060 | 58.70 | 30.20 | 11.10 | 0.031 |
| | Shaking for 3 days | Colorless and no visible foreign matter | 5.06 | 6.004 | 60.20 | 28.50 | 11.30 | 0.031 |
| Formulation 14 | T0 | Colorless and no visible foreign matter | 9.48 | 5.987 | 61.90 | 27.40 | 10.70 | 0.016 |
| | Shaking for 1 day | Colorless and no visible foreign matter | 9.37 | 6.000 | 61.90 | 27.60 | 10.50 | 0.016 |
| | Shaking for 3 days | Colorless and no visible foreign matter | 10.29 | 6.002 | 60.70 | 27.80 | 11.50 | 0.016 |
| Formulation 15 | T0 | Colorless and no visible foreign matter | 9.39 | 5.988 | 61.50 | 27.80 | 10.70 | 0.016 |
| | Shaking for 1 day | Colorless and no visible foreign matter | 9.34 | 6.020 | 61.60 | 28.00 | 10.50 | 0.016 |
| | Shaking for 3 days | Colorless and no visible foreign matter | 9.82 | 5.965 | 59.90 | 28.30 | 11.70 | 0.016 |
| Formulation 16 | T0 | Colorless and no visible foreign matter | 9.49 | 6.007 | 62.00 | 27.90 | 10.10 | 0.016 |

TABLE 4-continued

Summary of shaking stability results for the formulations with different ADC concentrations and polysorbate 80 concentrations

| Formulation number | Time point | Appearance | Protein concentration (mg/ml) | pH value | CEX-HPLC(%) Main peak | Acidic peak | Basic peak | AS269 residue (%) |
|---|---|---|---|---|---|---|---|---|
| | Shaking for 1 day | Colorless and no visible foreign matter | 9.61 | 5.988 | 60.70 | 28.70 | 10.60 | 0.016 |
| | Shaking for 3 days | Colorless and no visible foreign matter | 10.01 | 6.090 | 61.10 | 27.70 | 11.20 | 0.016 |
| Formulation 17 | T0 | Colorless and no visible foreign matter | 21.00 | 5.987 | 61.10 | 27.70 | 11.20 | 0.0078 |
| | Shaking for 1 day | Colorless and no visible foreign matter | 20.61 | 5.984 | 60.60 | 27.90 | 11.50 | 0.0078 |
| | Shaking for 3 days | Colorless and no visible foreign matter | 20.95 | 6.001 | 60.20 | 27.20 | 12.60 | 0.0078 |
| Formulation 18 | T0 | Colorless and no visible foreign matter | 20.73 | 6.002 | 60.90 | 28.10 | 11.00 | 0.0078 |
| | Shaking for 1 day | Colorless and no visible foreign matter | 21.70 | 6.034 | 60.30 | 28.10 | 11.60 | 0.0078 |
| | Shaking for 3 days | Colorless and no visible foreign matter | 21.39 | 5.993 | 61.60 | 26.10 | 12.30 | 0.0078 |
| Formulation 19 | T0 | Colorless and no visible foreign matter | 20.99 | 6.090 | 62.10 | 27.40 | 10.40 | 0.0078 |
| | Shaking for 1 day | Colorless and no visible foreign matter | 20.82 | 6.007 | 60.10 | 28.90 | 11.00 | 0.0078 |
| | Shaking for 3 days | Colorless and no visible foreign matter | 21.20 | 5.987 | 58.30 | 29.80 | 11.90 | 0.0078 |
| Formulation 20 | T0 | Colorless and no visible foreign matter | 30.67 | 6.002 | 60.20 | 28.80 | 10.90 | 0.0052 |
| | Shaking for 1 day | Colorless and no visible foreign matter | 29.72 | 6.030 | 56.60 | 30.30 | 13.10 | 0.0052 |
| | Shaking for 3 days | Colorless and no visible foreign matter | 30.02 | 5.988 | 60.00 | 28.30 | 11.70 | 0.0052 |
| Formulation 21 | T0 | Colorless and no visible foreign matter | 31.27 | 6.003 | 59.90 | 29.10 | 11.00 | 0.0052 |
| | Shaking for 1 day | Colorless and no visible foreign matter | 29.95 | 6.045 | 56.50 | 30.30 | 13.20 | 0.0052 |
| | Shaking for 3 days | Colorless and no visible foreign matter | 31.06 | 6.010 | 59.30 | 29.00 | 11.60 | 0.0052 |
| Formulation 22 | T0 | Colorless and no visible foreign matter | 30.29 | 5.978 | 60.60 | 28.60 | 10.70 | 0.0052 |
| | Shaking for 1 day | Colorless and no visible foreign matter | 29.92 | 5.980 | 56.80 | 31.60 | 11.50 | 0.0052 |
| | Shaking for 3 days | Colorless and no visible foreign matter | 30.11 | 6.002 | 59.40 | 28.80 | 11.80 | 0.0052 |

Example 3 Study on Freeze-Drying Parameters of the Formulations with Different Solid Contents Formulations 23-34 were designed to investigate the effect of different combinations of anti-HER2 ADC concentrations and trehalose concentrations on the freeze-drying parameter (Tg'/Tc). The results of Table 5 show that the freeze-drying parameters of the formulations with different combinations of anti-HER2 ADC concentrations and trehalose concentrations exist differences. Considering the influence of the freeze-drying parameter (Tg'/Tc), freeze-drying filling volume and anti-HER2 ADC concentration on freeze-drying appearance, process time and stability, the concentration of anti-HER2 ADC may be 10 mg/mL to 30 mg/ml and the concentration of trehalose may be 2.5% to 8%. Two formulations (formulation 23 and formulation 24), three formulations (formulation 27, formulation 28 and formulation 29) and one formulation (formulation 31) with anti-HER2 ADC concentration of 10 mg/ml, 20 mg/ml and 30 mg/ml respectively were taken to carry out freeze-drying. According to the results (Table 6), the freeze-dried product with formulation 28 has the best appearance performance.

TABLE 5

Summary of freeze-drying parameter results for the formulations with different solid contents

| Formulation Number | Buffer salt | pH value | Polysorbate 80 concentration | Trehalose concentration | Anti-HER2 ADC concentration | Solid content | Collapsing temperature (Tc) | Glass-transition temperature (Tg') |
|---|---|---|---|---|---|---|---|---|
| Formulation 23 | 5 mM histidine salt | 6.0 | 0.02% | 4.5% | 10 mg/ml | 5.5% | −24.0 | −28.56 |
| Formulation 24 | | | | 7% | | 8% | −24.5 | −30.31 |
| Formulation 25 | | | | 9% | | 10% | −25.0 | −31.21 |
| Formulation 26 | | | | 11% | | 12% | −26.0 | −31.08 |
| Formulation 27 | | | | 3.5% | 20 mg/ml | 5.5% | −20.0 | −25.24 |
| Formulation 28 | | | | 6% | | 8% | −22.5 | −26.11 |
| Formulation 29 | | | | 8% | | 10% | −22.5 | −26.99 |
| Formulation 30 | | | | 10% | | 12% | −24.3 | −26.52 |
| Formulation 31 | | | | 2.5% | 30 mg/ml | 5.5% | −15.6 | −24.59 |
| Formulation 32 | | | | 5% | | 8% | −17.7 | −25.50 |
| Formulation 33 | | | | 7% | | 10% | −21.0 | −25.94 |
| Formulation 34 | | | | 9% | | 12% | −19.0 | −26.11 |

TABLE 6

Summary of freeze-drying appearances for different formulations

| | Freeze-drying process | | | | Moisture |
|---|---|---|---|---|---|
| Formulation | Pre-freezing | Primary sublimation | Secondary sublimation | Appearance | content (%) |
| Formulation 23 | Prefreezing at −45° C. for 5 hours | Heating up to −30° C. at 5° C./h and holding for 40 hours with a vacuum degree of 12 Pa | Heating up to 25° C. at 11° C./h and holding for 3 hours with a vacuum degree of 12 Pa | Top cracking within 2 vials, top cracking and bottom shrinkage within 10 vials, bottom collapse within 1 vial and complete melting within 1 vial. | 1.520 |
| Formulation 24 | | | | Top cracking and bottom shrinkage within 11 vials, and bottom collapse within 3 vials. | 2.557 |
| Formulation 27 | | | | Surface cracking within 19 vials, and side collapse within 1 vial. | 0.878 |
| Formulation 28 | | | | Slight top cracking, slight bottom cracking and detachment within 20 vials. | 0.918 |
| Formulation 29 | | | | Surface cracking and detachment within 16 vials, and bottom shrinkage and detachment within 4 vials. | 0.889 |
| Formulation 31 | | | | Detachment and fragmentation within 29 vials. | 0.875 |

Example 4 Freeze-Drying Process Study

Formulation 28 of Example 3, that is, 20 mg/mL of anti-HER2 ADC (ARX788), 5 mM of histidine, 6 wt. % of trehalose and 0.02 wt. % of polysorbate 80, was used to investigate the freeze-drying process.

ADC samples and placebo (5 mM of histidine, 6 wt. % of trehalose and 0.02 wt. % of polysorbate 80) were prepared by referring to the sample preparation steps (1)-(4) in Example 1. The results are shown in Table 7. From the results of Table 7, it can be seen that the temperatures, vacuum degrees and other process parameters of primary sublimation and secondary sublimation will affect the appearance, moisture content and other properties of the obtained freeze-dried products. The appearances of the freeze-dried products obtained from process 1' are severely unqualified, and the moisture content is high, which is not conducive to preparation stability.

Although the appearances of the freeze-dried products obtained from process 1 have been significantly improved, there are still a certain proportion of unqualified products. For processes 2-4, the processes of primary and secondary sublimations are comprehensively considered and optimized, resulting in the freeze-dried products with excellent appearances and low moisture content, thus the yield and product stability of the freeze-dried preparation can be significantly improved.

TABLE 7

| Freeze-drying process study | | | | | | | | |
|---|---|---|---|---|---|---|---|---|
| Batch | | | Process-1' | Process-1 | Process-2 | Process-3 | Process-4 |
| Shelf area of freeze-dryer | | | 5 m² | 0.2 m² | 0.2 m² | 0.2 m² | 5 m² |
| Sample description | | | 123 vials of ADC, with the rest filled with placebos (2 shelves) | 108 vials of placebos | 5 vials of ADC, with the rest filled with placebos (2 shelves) | 20 vials of ADC, with the rest filled with placebos (2 shelves) | 27 vials of ADC, with the rest filled with placebos (2 shelves) |
| Pre-freezing method | | | Cooling down the shelf to 4° C. within 1 hour and holding at the same temperature for 1 hour, then cooling down the shelf to −45° C. within 3.5 hours and holding at the same temperature for 5 hours | | | | |
| Primary sublimation | Shelf temperature | | −30° C. | −30° C. | −20° C. | −23° C. | −23° C. |
| | Heating up time | | 7.5 h | 0.5 h | 0.5 h | 0.5 h | 0.5 h |
| | Holding time | | | | 40 h | | |
| | Vacuum degree | | 22 Pa | 13 Pa | 13 Pa | 13 Pa | 13 Pa |
| Secondary sublimation | Shelf temperature | | 25° C. | 25° C. | 30° C. | 25° C. | 25° C. |
| | Heating up time | | | | 5 h | | |
| | Holding time | | 5 h | 8 h | 8 h | 8 h | 8 h |
| | Vacuum degree | | 22 Pa | 13 Pa | 13 Pa | 13 Pa | 13 Pa |
| Test result | Appearance | | There are about 90% of ADC samples fail visual inspection, with partial shrinkage at the bottom of the vial wall and layering in the middle of the drug cake. | There is slight shrinkage at the bottom of the vial. 5 out of 108 vials are unqualified in appearance. | There is slight shrinkage at the edge. There are slight cracks at the bottom of the ADC and no cracks at the bottom of the placebo. All of them are qualified in appearance. | There is slight shrinkage at the edge. There are slight cracks at the bottom of the ADC and no cracks at the bottom of the placebo. All of them are qualified in appearance. | There is no shrinkage or layering in the middle of the drug cake in the ADC samples, part of which have cracks. All of them are qualified in appearance. |
| | Moisture content | | 1.738% (ADC) 1.823% (placebo) | 0.667% (placebo) | 0.545% (ADC) 0.533% (placebo) | 0.469% (ADC) 0.737% (placebo) | 0.717% (ADC) 0.898% (placebo) |
| | pH | | 5.996 | 6.034 | 5.989 | 6.012 | 6.019 |
| | ADC reconstitution time | | 30 s | 41 s | 43 s | 34 s | 21 s |
| | CEX | Main peak | 57.17% | 57.24% | 57.67% | 58.09% | 57.63% |
| | | Acidic peak | 26.39% | 26.30% | 25.89% | 25.39% | 25.52% |
| | | Basic peak | 16.44% | 16.46% | 16.44% | 16.52% | 16.85% |
| | SEC | Main peak | 95.90% | 95.47% | 96.00% | 96.13% | 95.72% |
| | | HMW | 4.10% | 4.53% | 4.00% | 3.87% | 4.28% |
| | | LMW | Not detected | Not detected | Not detected | Not detected | Not detected |
| | AS269 residue | | 0.017% | 0.016% | 0.016% | 0.016% | 0.015% |

Example 5 Pilot Scale Production and Stability Investigation

Three batches of pilot scale production were carried out according to process 4 determined in Example 4 (i.e., pilot scale batch −1 to pilot scale batch −3, with a batch size of approximately 1500 vials). The process was as follows:

(1) ADC drug substance was taken from the refrigerator 24 hours in advance and placed at room temperature for thawing. After the thawing was completed, the drug substance was merged into a Schott bottle, and stirred and mixed thoroughly.

(2) The mixed drug substance was sterilized and filtrated through a two-stage 0.22 μM sterile filter into a sterile storage bag.

(3) Penicillin vials were sterilized through a tunnel drying oven and delivered to an isolator, and rubber stoppers and aluminum covers were delivered to the isolator through an RTP bucket after steam sterilization.

(4) The sterile storage bag was connected to the isolator through a sterile connection, then the solution was filled into the sterilized penicillin vials.

(5) The penicillin vials were semi-stoppered, and then transferred to a freeze-dryer, in which the shelves needed to be all filled, and the vacancy needed to be filled with empty penicillin vials. The program for freeze-drying was started, and after the freeze-drying was completed, the vials were full-stoppered.

(6) After being full-stoppered, the penicillin vials were taken out of the freeze-dryer and delivered to a capping area for capping.

(7) After capping, the penicillin vials were subjected to outer surface cleaning, visual examination, labelling and packaging.

Production data shows that all three batches of the production are successfully completed, and the freeze-dried products are white or off-white blocks in appearance. The yield of finished products is high, and there are no defective products like remelting or collapse. All the reconstitution time is less than 1 minute, and all the moisture contents are less than or equal to 1%.

For the sterile powder for injection produced by the method described in this example, the stability of the three batches of samples under long-term (5±3° C.) conditions for 24 months and accelerated (25±2° C.) conditions for 6 months was evaluated by using appearance, pH value, reconstitution time, moisture content, protein content, drug-antibody ratio, SEC, CEX, CE-SDS, AS269 residue, cell-based potency, binding potency, etc. as indicators. The results show that there are no significant changes in all indicators before and after the evaluation.

Meanwhile, one batch of the samples (pilot scale batch −2) was subjected to high-temperature impact factor investigation. The results show that the samples have very good stability, even after a 6-month evaluation at 40° C., the change ranges of CEX peak (FIG. 2A) and potency (FIG. 2B) both are very small.

Unless otherwise particularly limited, the terms used in the present invention are commonly used meanings understood by those skilled in the art.

The embodiments described in the present invention are for illustrative purposes only and are not intended to limit the scope of protection of the present invention. Those skilled in the art may make various other substitutions, changes, and improvements within the scope of the present invention. Therefore, the present invention is not limited to the aforementioned embodiments but is only limited by the claims.

What is claimed is:

1. A freeze-dried composition containing anti-HER2 drug conjugate, wherein the freeze-dried composition comprises 10 mg/mL to 30 mg/mL of ARX788, 5 mM to 10 mM of histidine, 2.5 wt. % to 8 wt. % trehalose and 0.01 wt. % to 0.05 wt. % of polysorbate 80, wherein the pH value of the freeze-dried composition is from 6.0 to 6.3.

2. A freeze-dried preparation containing anti-HER2 drug conjugate, wherein the freeze-dried preparation is prepared from the freeze-dried composition according to claim 1.

3. A preparation method for a freeze-dried preparation of the freeze-dried composition according to claim 1, comprising the following steps:

S1: prefreezing the freeze-dried composition at −50° C. to −40° C. for 3 hours to 6 hours;

S2: heating up the freeze-dried composition after treated in step S1 to −25° C. to −20° C. and holding at this temperature and a vacuum degree of 10 Pa to 15 Pa for 30 hours to 50 hours; and S3: heating up the freeze-dried composition after treated in step S2 to 25° C. to 30° C. and holding at this temperature and a vacuum degree of 10 Pa to 15 Pa for 5 hours to 10 hours.

4. The preparation method according to claim 3, wherein the step S1 comprises: cooling down the freeze-dried composition to 2° C. to 5° C. within 0.5 hour to 1.5 hours and holding at the same temperature for 0.5 hour to 1.5 hours, then cooling down to −50° C. to −40° C. within 3 hours to 5 hours and holding for 3 hours to 6 hours at the same temperature.

5. The preparation method according to claim 3, wherein the step S2 comprises: heating up the freeze-dried composition after treated in step S1 to −23° C. to −20° C. within 0.2 hour to 0.8 hour and holding at the same temperature and a vacuum degree of 12 Pa to 14 Pa for 35 hours to 45 hours.

6. The preparation method according to claim 3, wherein the step S3 comprises: heating up the freeze-dried composition after treated in step S2 to 25° C. to 30° C. within 2 hours to 8 hours and holding at the same temperature and a vacuum degree of 12 Pa to 14 Pa for 5 hours to 10 hours.

7. A method for treating a cancer by administering the freeze-dried composition according to claim 1 or a freeze-dried preparation thereof, to a subject in need, wherein the cancer is breast cancer, gastric cancer, lung cancer, ovarian cancer, colorectal cancer, urothelial cancer, biliary tract cancer, liver cancer, brain cancer, esophageal cancer, endometrial cancer, uterine cancer, kidney cancer, bladder cancer, thyroid cancer, salivary gland cancer or pancreatic cancer.

8. The freeze-dried composition according to claim 1, wherein the pH value of the freeze-dried composition is 6.0.

9. The freeze-dried composition according to claim 8, wherein the freeze-dried composition comprises 20 mg/mL of ARX788, 5 mM of histidine, 6 wt. % trehalose and 0.02 wt. % of polysorbate 80.

10. A freeze-dried preparation containing anti-HER2 drug conjugate, wherein the freeze-dried preparation is prepared from the freeze-dried composition according to claim 9.

11. A method for treating a cancer by administering the freeze-dried composition of claim 8 or the freeze-dried preparation thereof, to a subject in need, wherein the cancer is breast cancer, gastric cancer, lung cancer, ovarian cancer, colorectal cancer, urothelial cancer, biliary tract cancer, liver cancer, brain cancer, esophageal cancer, endometrial cancer, uterine cancer, kidney cancer, bladder cancer, thyroid cancer, salivary gland cancer or pancreatic cancer.

12. A method for treating a cancer by administering the freeze-dried composition of claim 9 or the freeze-dried preparation thereof, to a subject in need, wherein the cancer is breast cancer, gastric cancer, lung cancer, ovarian cancer, colorectal cancer, urothelial cancer, biliary tract cancer, liver cancer, brain cancer, esophageal cancer, endometrial cancer, uterine cancer, kidney cancer, bladder cancer, thyroid cancer, salivary gland cancer or pancreatic cancer.

* * * * *